US012023418B2

(12) United States Patent
Almarza et al.

(10) Patent No.: US 12,023,418 B2
(45) Date of Patent: Jul. 2, 2024

(54) BIOCOMPATIBLE POLYMER AND MAGNESIUM FOR REGENERATION OF ARTICULAR SURFACES IN THE TEMPOROMANDIBULAR JOINT

(71) Applicant: UNIVERSITY OF PITTSBURGH—OF THE COMMONWEALTH SYSTEM OF HIGHER EDUCATION, Pittsburgh, PA (US)

(72) Inventors: Alejandro Almarza, Pittsburgh, PA (US); Adam Chin, Pembroke Pines, FL (US); Juan Taboas, Pittsburgh, PA (US); Yadong Wang, Ithaca, NY (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 415 days.

(21) Appl. No.: 16/330,538

(22) PCT Filed: Sep. 11, 2017

(86) PCT No.: PCT/US2017/050882
§ 371 (c)(1),
(2) Date: Mar. 5, 2019

(87) PCT Pub. No.: WO2018/049293
PCT Pub. Date: Mar. 15, 2018

(65) Prior Publication Data
US 2021/0275725 A1    Sep. 9, 2021

Related U.S. Application Data

(60) Provisional application No. 62/385,363, filed on Sep. 9, 2016.

(51) Int. Cl.
| A61L 27/46 | (2006.01) |
| A61L 27/38 | (2006.01) |
| A61L 27/44 | (2006.01) |
| A61L 27/56 | (2006.01) |

(52) U.S. Cl.
CPC ......... *A61L 27/446* (2013.01); *A61L 27/3817* (2013.01); *A61L 27/56* (2013.01); *A61L 2430/24* (2013.01)

(58) Field of Classification Search
CPC .... A61L 27/446; A61L 27/3817; A61L 27/56; A61L 2430/24
See application file for complete search history.

(56) References Cited

U.S. PATENT DOCUMENTS

| 2007/0202084 A1* | 8/2007 | Sadozai | A61K 9/0024 |
| | | | 514/54 |
| 2009/0196901 A1 | 8/2009 | Guilak et al. | |
| 2010/0285090 A1 | 11/2010 | Sevrain et al. | |
| 2011/0054629 A1* | 3/2011 | Seok | A61L 27/58 |
| | | | 623/23.6 |
| 2012/0237586 A1* | 9/2012 | Okamoto | A61L 27/3645 |
| | | | 424/423 |

FOREIGN PATENT DOCUMENTS

| WO | 2015142631 A1 | 9/2015 | |
| WO | WO-2015142631 A1 * | 9/2015 | ........... A61L 29/148 |

OTHER PUBLICATIONS

Brown et al. (Acta Biomaterialia 2015;11:543-553 available online Sep. 16, 2014). (Year: 2014).*
Hagandora et al. (Tissue Engineering: Part A. 2013; 19(5 and 6);729-737) (Year: 2013).*
Hagandora et al. (Annals of Biomedical Engineering 2012;40(3):688-696) (Year: 2012).*
Hagandora, CK. (Dissertation 2014, [online] retrieved from: http://d-scholarship.pitt.edu/22122/; 185 pages) (Year: 2014).*
Moioli et al. (Advanced Drug Delivery Reviews 2007;59:308-324) (Year: 2007).*
Ueki et al. (Journal of Cranio-Maxillofacial Surgery 2003;31:107-114). (Year: 2003).*
Hagandora, A Multi-Phase Approach To Tissue Engineering of the Temporomandibular Joint, University of Pittsburgh Swanson School of Engineering (Jul. 11, 2014).
International Search Report Issued in International Patent Application No. PCT/US2017/050882 dated Nov. 13, 2017.

* cited by examiner

*Primary Examiner* — Ernst V Arnold
(74) *Attorney, Agent, or Firm* — Carol A. Marmo; Eckert Seamans Cherin & Mellott, LLC

(57) ABSTRACT

The invention relates to biodegradable, biocompatible materials to promote regeneration of articular surfaces in the temporomandibular joint and, more particularly, to biomaterials and methods for facilitating fibrochondrocyte and chondrocyte growth in in-vitro and in-vivo environments. The materials include magnesium in solid form and polymer. The materials are effective to grow and regenerate fibrochondrocyte and chondrocyte cells, and restore bone cells.

5 Claims, No Drawings

BIOCOMPATIBLE POLYMER AND MAGNESIUM FOR REGENERATION OF ARTICULAR SURFACES IN THE TEMPOROMANDIBULAR JOINT

CROSS-REFERENCE TO RELATED APPLICATIONS

This application is a U.S. National Stage Application under 35 U.S.C. § 371 of PCT International Application No. PCT/US2017/050882, filed on Sep. 11, 2017, entitled "BIOCOMPATIBLE POLYMER AND MAGNESIUM FOR REGENERATION OF ARTICULAR SURFACES IN THE TEMPOROMANDIBULAR JOINT," which claims priority under 35 U.S.C. § 119(e) from U.S. provisional patent application No. 62/385,363, entitled "BIOCOMPATIBLE POLYMER AND MAGNESIUM FOR REGENERATION OF ARTICULAR SURFACES IN THE TEMPOROMANDIBULAR JOINT," filed on Sep. 9, 2016, the contents of which are incorporated herein by reference.

GOVERNMENT SUPPORT AND FUNDING

This invention was made with government support under grant number EEC 0812348 awarded by the National Science Foundation (NSF), and grant number AR 062598 awarded by the National Institutes of Health (NIH). The government has certain rights in the invention.

FIELD OF THE INVENTION

The invention relates to biodegradable, biocompatible materials to promote regeneration of articular surfaces in the temporomandibular joint and, more particularly, to biomaterials and methods for facilitating fibrochondrocyte and chondrocyte growth in in-vitro and in-vivo environments.

BACKGROUND OF THE INVENTION

Temporomandibular joint disorder (TMJD) encompasses a wide spectrum of clinical conditions involving the components of the temporomandibular joint (TMJ). The etiological causes of TMJD are largely unknown due to the large number of suspected cause triggers and their multi-factorial nature.

It is estimated that 10-36 million Americans are affected by TMJD. The symptoms and side effects of TMJD can vary from mild pain and clicking of the joint, to chronic pain, limited jaw motion and total degeneration. Traditional solutions range from performing arthroscopy to a total joint replacement in more serious cases. These limited solutions are due to the joint being avascular, as well as the inability of the fibrocartilage found in the TMJ disc and the condylar cartilage to regenerate.

The TMJ is a bilateral joint, which consists of the articulation of the condyle of the mandible with the articular eminence and glenoid fossa of the temporal bone. A fibrocartilage disc (i.e., TMJ disc) rests between this articulation and is involved with compressive, shear, and tensile loading of the joint during movement of the mandible. Similar to other synovial joints, TMJD can include displacement of the TMJ disc, and degeneration of the mandibular condylar cartilage and subchondral bone. A significant percentage of individuals that suffer from TMJD are affected with damage of the mandibular condylar cartilage (MCC) and subchondral bone. Further, it has been observed that up to 11% of individuals with TMJD have symptoms of TMJ osteoarthritis, which is often referred to as the wear and tear of the articulating surface of the condyle. Recapitulation of this fibrocartilage/bone interface of the surface of the condyle may provide return function.

A recent survey of more than 1,500 TMJD patients reported a surgical intervention rate of greater than 25%. Of these patients, many reported undergoing multiple surgical procedures to correct TMJD. It was reported that 54% of patients had one to three surgical procedures, 30% of patients had four to nine procedures, and 16% of patients had undergone ten or more surgical procedures to correct TMJD. Patients reported low satisfaction with the outcomes of these surgical procedures. Of those undergoing arthroplasty, 6% of patients reported significant improvement, 32% of patients reported some improvement, 28% of patients reported no change, and 46% of patients reported being worse or significantly worse following surgery. These reports demonstrate a need for a better solution to meniscus removal without replacement. As a result, surgeons are generally opting to perform arthroplasty promptly to avoid the patient undergoing so many procedures.

Thus, there is a need in the art to develop improved solutions for TMJD. It is an objective of the invention to promote regeneration of the avascular environment of the TMJ by developing a material capable of hosting native cells, e.g., fibrochondrocytes, for use as a TMJ medical implant device. Further, in addition to being biocompatible, it is desired that the material be biodegradable, such that surgery is not required to remove the medical implant device when it is no longer needed or useful.

SUMMARY OF THE INVENTION

In one aspect, the invention provides a temporomandibular joint medical implant device that includes a composite material, which includes polymer and magnesium in a solid form. The temporomandibular joint medical implant device is effective to grow and regenerate fibrochondrocyte and chondrocyte cells, and to restore bone cells.

The polymer can be poly(glycerol sebacate). The magnesium can be selected from elemental magnesium, magnesium-containing compounds, magnesium alloys, salts thereof, and mixtures and combinations thereof. The solid form of the magnesium can be selected from magnesium particles, magnesium powder, magnesium ceramic, metallic magnesium, such as, sheet and/or mesh, and combinations or mixtures thereof. The magnesium may form a magnesium-containing solution. In certain embodiments, the magnesium is combined with seeding cells selected from fibrochondrocyte and chondrocyte cells. The magnesium, e.g., magnesium-containing solution, can be media for use in culturing the seeding cells.

The polymer can be in a matrix form. The magnesium can be deposited on the exterior, or within the interior, of the polymer matrix. For example, the magnesium can form a layer or coating on an external surface of the polymer matrix. Alternately, or additionally, the magnesium can be located, e.g., embedded, dispersed, absorbed or the like, below the external surface and within the interior of the polymer matrix.

The device can be biphasic, including a polymer phase and a magnesium phase.

In certain embodiments, the magnesium is in the form of a mesh or sheet. The mesh or sheet can be applied to the external surface of the polymer matrix or, alternatively, the mesh or sheet can be located below the external surface, within the interior, of the polymer matrix.

The temporomandibular joint medical implant device can be in the form of a scaffold. The scaffold can include a sponge composed of the polymer and a gelatin, and the sponge can be soaked with the magnesium-containing solution.

In another aspect, the invention provides a method of preparing the temporomandibular joint medical implant device. The method includes forming a composite material, which includes polymer and magnesium in a solid form, and implanting said composite material in the temporomandibular joint, wherein the temporomandibular joint medical implant device is effective to grow and regenerate fibrochondrocyte and chondrocyte cells, and restore bone cells.

In certain embodiments, the composite material is formed by combining, e.g., mixing or blending, the magnesium and polymer to form a mixture or blend. The magnesium may be dispersed or embedded in the polymer, e.g., polymer matrix. Alternately, the magnesium may be applied to, or deposited on, an external surface of a polymer matrix. Still, alternately, the magnesium in the form of a sheet or mesh may be located or positioned within the interior of a polymer matrix.

In certain embodiments, the polymer can be in the form of a gelatin hydrogel or sponge, and the magnesium can be incorporated, e.g., absorbed, by soaking the polymer sponge in the magnesium-containing solution.

The implanting of the composite material can be beneath the condylar fibrocartilage to effect regeneration of bone and cartilage interface of mandibular condyle.

Further, the forming of the composite material can include combining the magnesium with seeding fibrochondrocyte and chondrocyte cells.

DETAILED DESCRIPTION OF THE PREFERRED EMBODIMENTS

The invention relates to biocompatible, biodegradable materials for addressing temporomandibular joint disorder (TMJD). In accordance with the invention, the biomaterials are capable of hosting native cells of the TMJ and growing new cells, such as to promote regeneration of the avascular environment of the TMJ. The native cells include fibrochondrocytes and chondrocytes. The invention also relates to methods of making the biocompatible, biodegradable materials, and medical implant devices, e.g., scaffolds, containing the biocompatible, biodegradable materials.

It has been found that tissue engineering approaches with biodegradable polymeric scaffolds can by employed to regenerate the temporomandibular joint (TMJ) tissues. In certain embodiments, soft polymer materials, e.g., poly(glycerol sebacate) (PGS) and gelatin that form polymeric scaffold sponges, provide a substrate for cell infiltration and remodeling. Magnesium may be incorporated into the soft polymer, e.g., gelatin hydrogels or sponges, as a bioactive signal.

The invention provides the benefit of being effective to heal (e.g., simultaneously) both of the bone and the cartilage of the bone-cartilage interface, of the mandibular condyle. The polymer serves as a host to native fibrochondrocytes to assist in fibrocartilage regeneration of the cartilage portion. Concurrently, the osteoconductive nature of the magnesium in the scaffold restores the bone portion.

Thus, in accordance with the invention, a single composite material or a single medical implant device made therefrom is capable of simultaneously healing bone and cartilage of the bone-cartilage interface of the mandibular condyle.

The invention also provides the capability of restoring the TMJ to its native properties, instead of relying on an apparatus as a replacement in the event of joint degeneration. Thus, the need for revision surgeries or the risks of complications associated with prosthetics, such as immune response, are precluded.

Biomaterials for use in the invention include a combination of magnesium in a solid form and polymer. The polymer for use in the invention is selected from a variety of polymers that are known in the art to exhibit both biocompatibility and biodegradability. Non-limiting examples of suitable polymers include, but are not limited to, calcium phosphate, hydroxyapatite, lecithin, collagen, fibrin, gelatin, silk, elastin, chitosan, starch, alginate, hyaluronic acid, chondroitin, agarose, cellulose, polyester, such as, poly(glycolic acid) (PGA), poly(L-lactic acid) (PLA), poly(lactic-co-glycolic acid) (PLGA), poly(caprolactone) (PCL), poly(propylene fumarate), polyorthoester, polyanhydride, poly(ethylene glycol) (PEG), polycarbonate, polyurethane, elastomer, such as but not limited to poly(glycerol sebacate) (PGS), and mixtures thereof. In certain embodiments, poly(glycerol sebacate) is preferred.

The magnesium can be selected from elemental magnesium, magnesium-containing compounds, magnesium alloy and salts thereof. The solid form of the magnesium can include, but is not limited to, particle/particulate magnesium, powder magnesium, magnesium ceramic, metallic magnesium, and combinations and mixtures thereof. The metallic magnesium can be in the form of a sheet and/or a mesh. In certain embodiments, the magnesium is provided in the form of magnesium chloride, magnesium phosphate, magnesium sulfate, and mixtures thereof.

The magnesium can be applied to, or deposited on, an external surface of the polymer, e.g., polymer matrix. For example, the magnesium in solid form can be incorporated, e.g., dispersed, mixed or blended, into a coating composition, e.g., mixture of blend, that is applied to or deposited on an external surface of the polymer matrix, e.g., scaffold. Alternately, or additionally, the magnesium in solid form can be dispersed and/or embedded below the external surface of the polymer matrix. For example, magnesium and polymer can be combined, e.g., mixed or blended, to form a magnesium/polymer composition, e.g., mixture or blend. This resulting composition can form the resulting composite, e.g., scaffold, wherein the magnesium is dispersed within, e.g., throughout, a polymer matrix. Wherein the magnesium is in the form of a sheet or mesh, the magnesium can be located or positioned within the interior of a polymer matrix. A magnesium/polymer composite can be formed such that a polymer matrix forms top and bottom surfaces and the magnesium sheet or mesh is positioned, e.g., "sandwiched", there between. Furthermore, there may be multiple, alternating layers of polymer and magnesium sheet or mesh.

Moreover, as previously described herein, in certain embodiments, polymer in the form of a gelatin hydrogel or sponge, e.g., a poly(glycerol sebacate) (PGS) and gelatin polymeric scaffold sponge, provides a substrate for cell infiltration and remodeling. The magnesium in the form of a solution, e.g., saturated magnesium phosphate solution, can be absorbed or soaked into the sponge, and subsequently implanted or inserted into a TMJ defect in a patient during a surgical procedure.

Optionally, the magnesium can be combined with seeding cells, e.g., fibrochondrocyte and/or chondrocyte cells, such that these cells are present on the external surface of the polymer matrix or within the interior of the polymer matrix. In certain embodiments, these cells are incorporated into the polymer matrix by absorption, e.g., soaking of magnesium solution into a polymer-gelatin sponge. For example, fibrochondrocyte and/or chondrocyte cells are allowed to culture in media that includes the magnesium, and then seeded, e.g., by injection, soaking, absorption, or the like, into the polymer matrix, e.g., polymer-gelatin sponge.

There is an interest in designing and developing biodegradable materials because after a period of time, the implant device is no longer needed, e.g., after bone or tissue healing is complete. The device can be left in situ or, alternatively, can be removed. Each of these alternatives has disadvantages associated therewith. For example, leaving the device in situ increases the chances of infection and rejection, and removal of the device requires a second surgery and causes a risk of infection, pain and discomfort to the patient, as well as it being an additional expense. A resorbable polymeric device that is effective to degrade over a period of time, e.g., by dissolving in the physiological environment, can overcome the aforementioned disadvantages. Thus, the device does not remain in-situ and there is no need to surgically remove the device when the device is no longer needed. However, resorbable polymeric materials can lack mechanical strength as compared to that exhibited by metal implants. As a result, the combination of polymer with magnesium is advantageous.

Magnesium and its alloys have mechanical properties compatible to bone and tissue, and can be resorbed over a period of time. For example, magnesium is very lightweight, has a density similar to cortical bone, has an elastic modulus also close to natural bone, is essential to human metabolism, is a cofactor for many enzymes, and stabilizes the structures of DNA and RNA. As for the magnesium, it has been demonstrated in the art that this elemental metal and its alloys exhibit both biocompatibility and biodegradability. For example, magnesium and its alloys have been shown to promote both bone and cartilage independently. Further, it has been demonstrated that degrading magnesium scaffolds promote both bone formation and resorption. When examining the effect of magnesium on cartilage, high magnesium concentrations can increase the proliferation and re-differentiation of chondrocytes.

In accordance with the invention, the polymer and magnesium are selected such that their combination provides a biomaterial that is capable of facilitating fibrochondrocyte and chondrocyte growth in an in-vitro or in-vivo environment, in the presence or absence of seeded cells. In addition, these materials are capable of regenerating bone and tissue in the avascular environment of the TMJ.

The polymer is capable of hosting native fibrochondrocytes to contribute to regeneration of fibrocartilage in the avascular environment of the TMJ and simultaneously, the osteoconductive nature of the magnesium is capable of restoring the bone portion affected by a TMJD. The polymer/magnesium materials of the invention provide the benefit of healing the bone and cartilage interface of the mandibular condyle.

In certain embodiments, the invention includes a biphasic matrix, e.g., scaffold, wherein a first polymer phase is effective to regenerate fibrocartilage on the cartilage portion of the bone/cartilage interface, and a second magnesium phase is effective to restore bone on the bone portion of said interface. For example, one half of a biphasic scaffold can be composed of PGS and the other half can be composed of magnesium. A lower longitudinal portion or layer of the scaffold may be composed of magnesium ceramic and an upper longitudinal portion or layer of the scaffold may be composed of the PGS. The magnesium portion can be used to anchor the structure to an implant site. Thus, the magnesium serves two purposes: (i) to enhance osteointegration, and (ii) to anchor the scaffold to the defect.

As previously mentioned, the scaffold, e.g., soft scaffold, may include the presence or absence of seeded fibrochondrocyte and/or chondrocyte cells. Further, other known components and additives may be included in the polymer/magnesium materials, e.g., composites, of the invention to impart additional characteristics and properties to the resulting scaffolds constructed therefrom.

In general, preparation of the polymer/magnesium matrices or composites of the invention include selecting the polymer, e.g., PGS, and magnesium in solid form, e.g., elemental magnesium, magnesium alloy, or metallic magnesium, e.g., a sheet or mesh, and combining the magnesium, e.g., magnesium solution, with the polymer by applying, mixing, blending, embedding, layering, absorbing, soaking or the like, the magnesium on/in the polymer.

The polymer/magnesium scaffolds of the invention can be prepared using various conventional methods and processes known in the art. In general, pressing, sintering and solvent casting with salt leaching methods can be employed. It is believed that the particular process used for casting may affect the properties and characteristics of the cast composite. In certain embodiments, the casting may be performed under a protective atmosphere to preclude, minimize or reduce decomposition of components in the composite. The protective atmosphere can include compounds selected from those known in the art, such as but not limited to, argon, sulfur hexafluoride and mixtures thereof. In further embodiments, the resulting cast can be subjected to various forming and finishing processes known in the art. Non-limiting examples of such processes include, but are not limited to, extrusion, forging, polishing (by mechanical and/or chemical means), surface treating (to form a superficial layer on the surface) and combinations thereof.

In accordance with certain embodiments, soft scaffolds are made by forming polymer, e.g., PGS, and gelatin into a sponge. Prior to implantation, these soft scaffolds, e.g., sponges, are soaked in a magnesium solution, e.g., magnesium phosphate solution. The magnesium soaked, polymer-gelatin soft scaffolds are then implanted in the mandibular condyle of a patient.

Additional objects, advantages and novel features of the invention may become apparent to one of ordinary skill in the art based on the following examples, which are provided for illustrative purposes and are not intended to be limiting.

EXAMPLES

An objective of the invention is to regenerate a TMJ with degeneration to its native state. There are no known methods of regenerative medicine to restore the TMJ. Various approaches were carried out to determine their efficacy in regenerating an osteochondral defect. The methods included the use of a regenerative polymer, and magnesium (a biodegradable metal) to anchor the polymer. These biomaterials were used to produce scaffolds, and the scaffolds were inserted into osteochondral defects of the mandibular condyle in skeletally mature goats. A caprine model was chosen due to the accessibility of the TMJ as opposed to the more commonly used porcine model. The scaffolds and condyles were evaluated following twelve weeks of healing.

In general, the objectives of the experiments conducted were as follows:
1. To assess the interaction of magnesium ions with PGS scaffold for promoting fibrochondrocyte growth;

2. To determine the efficacy of PGS and magnesium as a means of regenerating the bone and cartilage interface of the mandibular condyle; and
3. To determine the feasibility of using soft biomaterial scaffolds for regeneration of the fibrocartilage and subchondral bone of the TMJ.

Example 1—Assess the Interaction of Magnesium Ions with PGS Scaffold for Promoting Fibrochondrocyte Growth Scaffold Fabrication: Small discs were cut from PGS sheets using a 4 mm-diameter biopsy punch.

Method: Fibrochondrocytes were isolated from the costal rib of a goat. After three passages, these cells were then seeded to the PGS scaffolds via injection with a 23-gauge needle. There was created five different media for comparison. A chondrogenic media was made as a positive control. Four chondrogenic media were also prepared. Each contained 10 mM of one of the following chemicals: NaCl, Mg chloride, Mg phosphate, Mg sulfate. The cells were then allowed to culture for four weeks.

Analysis: A compressive stress relation test was used to determine the mechanical properties of the scaffolds. In addition, biochemistry was also performed to quantify the amount of collagen that was in each scaffold. A glycosaminoglycan assay was performed to quantify the GAG in the scaffolds in the future.

Results: Goat costal fibrochondrocytes were cultured in PGS for four weeks with control media and also media with different Mg ions. It appeared that the scaffolds treated with the Mg phosphate performed the best in terms of compression (peak stress). However, there were no statistically significant differences amongst the different media groups. Further analysis from the collagen assay showed no statistical difference between the Mg phosphate group and the control. Based on the results obtained, it appeared that the addition of Mg phosphate was beneficial when compared to the other chemicals based on the mechanical results. It was contemplated that a different control may be needed, instead of chondrogenic media, to pinpoint any positive effects that the Mg phosphate has on the fibrochondrocytes.

Example 2—Determine the Efficacy of PGS and Magnesium as a Means of Regenerating the Bone and Cartilage Interface of the Mandibular Condyle Scaffold Fabrication: A biphasic scaffold was created wherein half was pure PGS and the other half contained magnesium. A lower longitudinal portion or layer of the scaffold was composed of magnesium ceramic and an upper longitudinal portion or layer of the scaffold was composed of PGS. The scaffold had a radius of about 0.25 cm and a height of about 0.5 cm. The magnesium portion was used to anchor the structure to the implant site. Thus, the magnesium served two purposes: (i) to enhance osteointegration, and (ii) to anchor the scaffold to the defect. A cylindrical gelatin hydrogel scaffold was also inserted into the mandibular condyle.

The following groups were tested:
Empty defect;
Poly (glycerol sebacate) (PGS) alone;
PGS and Mg ceramic;
Gelatin methacrylate hydrogel; and
Gelatin methacrylate hydrogel and trimagnesium phosphate (TMP).

Method: A defect was made on top of the condyle of the mandible such that the defect was at the fibrocartilage and bone interface.

The animal model used for the study was a female, skeletally mature Spanish goat. There was easy access to the TMJ space of the goat. This particular animal model was used because it has some similar anatomy to the human mandible. The goat was chosen judiciously as it is the smallest animal with a TMJ that is accessible through normal surgery as a skeletally mature adult animal.

To create the osteochondral defect, a 1 mm-drill was used. A hole was drilled in the bone just under the condylar fibrocartilage. The hole was expanded to include the fibrocartilage surface. In this defect, the aforementioned groups were tested. A one-time point of twelve weeks was used to assess efficacy of PGS and magnesium to regenerate the bone and cartilage interface of the mandibular condyle.

Analysis: After twelve weeks, the goats were euthanized. Histology was used to observe sections of the mandibular condyle for fibrocartilage and bone. Hematoxylin and eosin was used to detect the presence of cell nuclei.

Results: The goats that underwent the procedure were 3-5 years old. A defect was successfully created on top of the condyle. Gross morphology of the PGS-only group showed a robust healing response. Also, the defect was made in the medial-lateral direction. New tissue was shown to have infiltrated the defect when the PGS-only scaffold was implanted. From the histology, the PGS group appeared to have performed the best, as there were cells, GAG and collagen present inside the osteochondral defect. The gelatin hydrogel showed a mixture of cell infiltration and fibrous tissue inside the defect. The gelatin hydrogel with TMP had no cell infiltration and was still in the process of degrading. This may be attributed to the placement of the defect and scaffold relative to the fibrochondrocyte layer.

Example 3—Determine the Feasibility of Using Soft Biomaterial Scaffolds for Regeneration of the Fibrocartilage and Subchondral Bone of the TMJ Materials and Methods: Skeletally mature (4-6 years old) female Spanish Boer goats were used for the surgeries. The goats were purchased from K Bar Livestock (Sabinal, TX). All of the animal procedures were performed in accordance with the National Institutes of Health guidelines for the use of laboratory animals.

Six goats were used. Four groups were evaluated: 1) an empty control, 2) PGS with Mg ions, 3) gelatin with Mg ions, and 4) gelatin with both Mg ions and trimagnesium phosphate (TMP) powder. As magnesium has been shown to have chondrogenic properties, it was hypothesized that its inclusion would facilitate cartilage formation in the defect. Thus, Mg salts were added to all the polymer groups, and was also delivered as a powder in the TMP group. Bilateral surgeries were performed on each goat. Thus, the total number of goat condyles analyzed was n=12. With four groups and twelve condyles, each group had a sample size of n=3. The same group was not performed on both condyles of the same animal.

Biomaterial Preparation: PGS was made into a sponge by leaching using particles of 75-150 µm, which have shown to facilitate fibroblast diffusion and attachment. Gelatin methacrylate scaffolds were made. A 10% gelatin hydrogel solution was made by mixing gelatin methacrylate with PBS at a 1:10 ratio. TMP (10 mM) was then added to this solution for the fourth group. 1 µL per 100 µL total solution of the photoinitiator, lithium phenyl-2,4,6-trimethylbenzoylphosphinate (LAP) solution, was added to the mixture. Gelatin scaffolds were then put under a UV light for photo-crosslinking. After the hydrogels were made, the scaffolds were lyophilized and put into an oven to bake at 100° C. to make them into sponges. Prior to implantation, scaffolds were soaked in a saturated (20% w/v) concentration of magnesium phosphate solution. In order to prepare the sponge scaffolds for insertion during surgery, the PGS scaffolds were soaked in ethanol and then autoclaved. The gelatin scaffolds were deemed sterilized because they went through the lyophilization and baking process.

Surgical Procedures: Surgeries were performed by first making an incision near the temporal lobe of the goat. Following the incision, the lateral pterygoid muscle along with others were separated to access the TMJ space. Once inside the joint space, 1-mm drill bit was used to create a trough-like defect on the superior surface of the mandibular condyle. This was performed while a spatula was situated between the drill and the TMJ disc to preserve the structural integrity of the rest of the joint. The drill was then inserted roughly 2-3 mm below the superior surface of the mandibular condyle, and allowed to enter the condyle to a depth of no more than 10 mm. Upon reaching this depth, the drill was then moved upward to remove the fibrocartilage layer superior to the subchondral bone. After making the osteochondral defect, the underlying muscles tissue was sutured. The skin was then sutured to completely close the incision. All animals were allowed to heal for 12 weeks, with an immediate return to a normal diet.

Histology: The mandibular condyles were retrieved immediately after 12 weeks of healing, and allowed to be fixed in 10% formalin overnight. Condyles from similarly aged female goats were obtained from K Bar Livestock for use as a native control. Samples were placed into 70% ethanol and immediately sent to Alizee Pathology (MA) for paraffin sectioning, and hematoxylin and eosin staining. Once the slides were returned, sections underwent Safranin-O for glysosaminoglycan (GAG) detection and Masson's Trichrome staining for collagen. Safranin-O/Fast green stains were done by first staining with Weigert's iron hematoxylin working solution and fast green solution. They were then rinsed in 1% acetic acid solution, and stained in 1% Safranin-O solution. As a result, this stain marked the cell nuclei black, the cytoplasm as green or gray, and mast cell granules, mucin, and cartilage as red. The trichrome stain was performed by first submerging slides into Weigert's hematoxylin. The slides were then placed into Bouin's solution to stain the background tissue red. Alinine blue was used last to stain the collagen blue. The collagen II immunostain, to visualize the cartilage layer, was done by using anti-human collagen type II produced in mouse (MP Biomedicals, Cat #: 008631711). The process was as follows: samples were first incubated overnight in a NA3PO4 buffer of pH 6 in an oven at 56° C., blocked with Avidin, blocked with Biotin, blocked with serum (with PBS washes between all steps), incubated with 1:1000 diluted Coll II overnight at 4° C., incubated with the secondary antibody (biotinylated anti mouse), incubated with ABC reagent (kit), applied AEC chromogen, and then counterstained with aqueous hematoxylin and Scott's Tap Water.

Results: The native condyle from two Spanish Boer goats, in hematoxylin and eosin images, exemplified the discrete layers of the mandibular condylar cartilage: the fibrous layer, the proliferative zone, the mature zone (area under the proliferative zone), and the hypertrophic zone. The safranin-O images showed glycosaminoglycan presence in the same zone as the hypertrophic cells for the same condyle. In the Masson's trichrome stain, there was a clear collagen layer beneath the fibrous layer of the native condyles.

The empty control on the first goat showed no signs of cell infiltration and only fibrous tissue surrounding the edges of the defect. The safranin-O image provided support with respect to the tissue being fibrous since there was no staining for GAG. There was a faint blue in the Masson's trichrome of the empty control condyle, which also suggested fibrous tissue growth over the defect. For the second goat, there also appeared to be fibrous tissue in-growth with bone remodeling in the fibrous scar. The third goat did not seem to have a full defect, and resembled the native condyle with a small tear in the condylar cartilage and a small hole in the subchondral bone.

The PGS group showed cellular infiltration within the osteochondral defect in the first goat. The safranin-O stain of the PGS-implanted scaffolds showed robust GAG presence at the site of the surgery. The Masson's trichrome demonstrated collagen formation inside the defect. In the second goat, the created defect was apparent, but the regeneration of the cartilage layer did not seem as robust as the first goat due to the majority of the tissue being fibrous; only a small amount of cells were present. Along the edges of the defect in the second goat, there was a very small amount of GAG, but still seemed to be mostly fibrous tissue; collagen was still seen in the defect. The third goat of the group had histological artifacts, but half of the defect was still visible with minor cell presence. There was no GAG, but there was a noticeable amount of collagen in the regenerated area.

There also seemed to be cellular infiltration in the gelatin scaffold group on the first goat, along with some portions of non-degraded scaffold. In addition, right above the cell layer of the regenerated tissues there appeared to be a fibrous layer—similar to that found in the native mandibular condylar cartilage. The same was seen for the safranin-O stain; fibrous tissue on the surface of the condyle with a GAG layer underneath it. The trichrome stain showed collagen as expected. The second condyle had with no in-growth of fibrous tissue. The third goat of the group had histological artifacts, but the drilled bone was still apparent in the sections as there was a small collection of cells in the right portion of the defect. GAG was seen in the same portion of the defect where the cells were. Judging from the trichrome stain, there was a mixture of fibrous tissue and collagen in the regenerated area.

The gelatin and TMP construct did not completely degrade by the end of 12 weeks. However, between the pores of the non-degraded scaffold, there appeared to be formation of neotissue as evidenced by the cells in each pore. The safranin-O and Masson's trichrome stains revealed mostly fibrous tissue between the pores of the scaffold. The second condyle of the group only had fibrous tissue growth in the defect. The condyle of the third goat was lost during histological processing.

Discussion: The adult porcine model has been considered as the gold standard model for TMJ anatomy. Based on conducting surgeries on the goat, this model provided improved benefits and was better suited for the purpose. From previous experience, the anatomy of the farm pig has proven to be a hindrance when it comes to executing repeatable procedures in the joint space. The zygomatic arch of the porcine model impedes access to the TMJ. This is where the caprine model was particularly beneficial, as the zygomatic arch prominence was minimal. In the Examples, it was easy to insert the drill into the surgical area and there was plenty of space between the glenoid fossa and the superior surface of the mandibular condyle.

Findings from the PGS group demonstrated the viability of the material of the invention as a means of cartilage regeneration in condylar defects. A large amount of cellular infiltration was observed with the presence of cartilage, with GAG and collagen in the same area. An immunostain for collagen II confirmed the type of collagen that regenerated in the osteochondral defect. Similar outcomes were observed with the gelatin scaffold group, as there were both GAG and collagen II within the defect. Although this group did not experience the same degree or level of cellular infiltration as the PGS group, it was observed that the fibrous layer was on top of the cellular layer, which is characteristic of the native TMJ mandibular condyle.

It is contemplated that magnesium metal (as opposed to ions) may be incorporated into these scaffolds to provide a better healing template for bone. The degree of subchondral bone regeneration could be due to the disparity of the mechanical properties of both the scaffold and the bone at the interface.

The healing responses observed with the gelatin-TMP scaffolds was much different than gelatin only. From the condyles in this particular group, all of them showed a non-degraded scaffold still lodged in the defect. An observation was made that the TMP group scaffolds were considerably stiffer than the gelatin-only scaffolds. In one condyle, the scaffold was stiff enough to prevent proper section of it; hence, there only being two available condyles of the TMP group for histology. It was contemplated that an ideal method of incorporating the magnesium would be to deliver them via microparticles as ions, in order to decrease the stiffness of the scaffold while also providing a more controlled delivery.

The need for a biodegradable polymer for TMJ regeneration is paramount. Total joint devices device come with the risk of revision surgery. An intervention that does not require secondary surgeries would be the most ideal treatment. From the histology results, it was shown that soft polymers such as gelatin and poly (glycerol sebacate) may be used as biomaterials for cartilage and fibrocartilage regeneration in the TMJ.

We claim:

1. A mandibular condyle bone-cartilage interface medical implant device, comprising:
    a single, biodegradable composite scaffold, comprising:
        a polymer sponge consisting of:
            gelatin methacrylate;
            poly(glycerol sebacate); and
            tri-magnesium phosphate powder; and
        magnesium phosphate solution absorbed or soaked into the sponge,
    wherein the single, biodegradable composite scaffold implanted into the bone-cartilage interface of the mandibular condyle simultaneously regenerates fibrocartilage on the cartilage portion and restores bone on the bone portion.

2. The mandibular condyle bone-cartilage interface medical implant device according to claim 1 further comprising magnesium particles, magnesium ceramic, metallic magnesium, and mixtures and combinations thereof.

3. The mandibular condyle bone-cartilage interface medical implant device according to claim 2 wherein the metallic magnesium is selected from the group consisting of a sheet and a mesh.

4. A method for regeneration of articular surfaces in the temporomandibular joint comprising:
    implanting the mandibular condyl bone-cartilage interface medical implant device according to claim 1 into the temporomandibular joint of a patient.

5. The method of claim 4, wherein the implanting step is beneath the condylar fibrocartilage to effect regeneration of a bone and cartilage interface of mandibular condyle.

* * * * *